United States Patent [19]
Takahashi et al.

[11] Patent Number: 5,032,511
[45] Date of Patent: Jul. 16, 1991

[54] DNA FRAGMENTS CODING FOR ANTIGENS SPECIFIC TO NON-A NON-B HEPATITIS, EXPRESSION VECTORS CONTAINING SAID DNA FRAGMENTS, TRANSFORMANTS AND PROCESS FOR PRODUCING SAID ANTIGENS

[75] Inventors: Kazuhiro Takahashi, Kyoto; Tatsurou Shibui, Machida; Michiru Kamizono, Machida; Rie Matsui, Machida; Yutaka Teranishi, Sagamihara; Shigetada Nakanishi, Kyoto; Naomi Kitamura, Moriguchi, all of Japan

[73] Assignee: Mitsubishi Kasei Corporation, Tokyo, Japan

[21] Appl. No.: 168,357

[22] Filed: Mar. 15, 1988

[30] Foreign Application Priority Data

Mar. 31, 1987 [JP] Japan .................................. 62-78313
Jun. 4, 1987 [JP] Japan ................................. 62-140586
Nov. 10, 1987 [JP] Japan ................................. 62-283990

[51] Int. Cl.$^5$ ...................... C12P 21/06; C12P 19/34; C12N 15/00; C12N 7/00; C12N 5/00; C12N 1/12; C12N 1/20; C12N 15/51; C07H 15/12; C07K 3/00
[52] U.S. Cl. ..................................... 435/69.1; 435/91; 435/112.3; 435/235.1; 435/240.1; 435/252.31; 435/252.33; 435/320.1; 536/27; 530/350; 935/18; 935/27; 935/31; 935/41; 935/56; 935/57; 935/65; 935/70; 935/73; 935/74; 935/81
[58] Field of Search .................. 435/68, 70, 91, 172.1, 435/172.3, 252.33, 320, 69.1, 235, 252.31; 536/27; 530/350; 935/18, 31, 41, 58, 65, 73, 81

[56] References Cited

FOREIGN PATENT DOCUMENTS 0066296 12/1982 European Pat. Off. .
0092249 10/1983 European Pat. Off. .
0154392 9/1985 European Pat. Off. .
0190972 8/1986 European Pat. Off. .
0263761 4/1988 European Pat. Off. .

OTHER PUBLICATIONS

Toshitaka, A. et al., Chemical Abstracts 007 105 p. 527, Abstract No. 151110y (1986).
Molecular Cloning, A Laboratory Manual Cold Spring Harbor Laboratory, CSH, NY (1982) p. 8.
Robinson, W. S., Virology PCA II: Hepatitis b Virus, pp. 1384–1386.
Hakim Naturwissenschaften, vol. 73, pp. 45–47 (1986).
European Search Report; (No. 88 40 0790).
Chemical Abstracts, vol. 105, No. 17, Oct. 1986, p. 527, No. 151110y.
Biological Abstracts, vol. 80, 1985, No. 4871, J. I. Tohmatsu et al.
Proc. Natl. Acad. Sci. USA, vol. 80, Mar. 1983, pp. 1194–1198, Young et al.

Primary Examiner—Richard A. Schwartz
Assistant Examiner—Joan Ellis
Attorney, Agent, or Firm—Foley & Lardner

[57] ABSTRACT

Provided herein are a DNA fragment which contains a base sequence coding for a non-A non-B hepatitis-specific antigenic protein occurring in cells of the liver affected with non-A non-B hepatitis, an expression vector in which said DNA fragment is inserted into a cloning site present downstream from a promoter thereof, a transformant obtained by introducing said expression vector into a host, and a process for producing said antigenic protein which comprises providing said expression vector, transforming a host with said expression vector, culturing the transforming host and collecting the protein produced therein.

12 Claims, 15 Drawing Sheets

Fig. 1a

```
         10              20              30
5' ATG GCA GTG ACA ACT CGT TTG ACA TGG TTG
3'

40              50              60
   CAT GAA AAG ATC CTG CAA AAT CAT TTT GGA 70              80              90
   GGG AAG CGG CTT AGC CTT CTC TAT AAG GGT 100             110             120
   AGT GTC CAT GGA TTC CAT AAT GGA GTT TTG 130             140             150
   CTT GAC AGA TGT TGT AAT CAA GGG CCT ACT 160             170             180
   CTA ACA GTG ATT TAT AGT GAA GAT CAT ATT 190             200             210
   ATT GGA GCA TAT GCA GAA GAG GGT TAC CAG 220             230             240
   GAA AGA AAG TAT GCT TCC ATC ATC CTT TTT 250             260             270
   GCA CTT CAA GAG ACT AAA ATT TCA GAA TGG 280             290             300
   AAA CTA GGA CTA TAT ACA CCA GAA ACA CTG
```

Fig. 1b

```
           310             320             330
TTT TGT TGT GAC GTT GCA AAA TAT AAC TCC 340             350             360
CCA ACT AAT TTC CAG ATA GAT GGA AGA AAT 370             380             390
AGA AAA GTG ATT ATG GAC TTA AAG ACA ATG 400             410             420
GAA AAT CTT GGA CTT GCT CAA AAT TGT ACT 430             440             450
ATC TCT ATT CAG GAT TAT GAA GTT TTT CGA 460             470             480
TGC GAA GAT TCA CTG GAC GAA AGA AAG ATA 490             500             510
AAA GGG GTC ATT GAG CTC AGG AAG AGC TTA 520             530             540
CTG TCT GCC TTG AGA ACT TAT GAA CCA TAT 550             560             570
GGA TCC CTG GTT CAA CAA ATA CGA ATT CTG 580             590             600
CTG CTG GGT CCA ATT GGA GCT GGG AAG TCT
```

Fig. 1c

```
        610             620             630
AGC TTT TTC AAC TCA GTG AGG TCT GTT TTC 640             650             660
CAA GGG CAT GTA ACG CAT CAG GCT TTG GTG 670             680             690
GGC ACT AAT ACA ACT GGG ATA TCT GAG AAG 700             710             720
TAT AGG ACA TAC TCT ATT AGA GAC GGG AAA 730             740             750
GAT GGC AAA TAC CTG CCA TTT ATT CTG TGT 760             770             780
GAC TCA CTG GGG CTG AGT GAG AAA GAA GGC 790             800             810
GGC CTG TGC ATG GAT GAC ATA TCC TAC ATC 820             830             840
TTG AAC GGT AAC ATT CGT GAT AGA TAC CAG 850             860             870
TTT AAT CCC ATG GAA TCA ATC AAA TTA AAT 880             890             900
CAT CAT GAC TAC ATT GAT TCC CCA TCG CTG
```

Fig. 1d

```
           910           920           930
AAG GAC AGA ATT CAT TGT GTG GCA TTT GTA 940           950           960
TTT GAT GCC AGC TCT ATT GAA TAC TTC TCC 970           980           990
TCT CAG ATG ATA GTA AAG ATC AAA AGA ATT 1000          1010          1020
CGA AGG GAG TTG GTA AAC GCT GGT GTG GTA 1030          1040          1050
CAT GTG GCT TTG CTC ACT CAT GTG GAT AGC 1060          1070          1080
ATG GAT CTG ATT ACA AAA GGT GAC CTT ATA 1090          1100          1110
GAA ATA GAG AGA TGT GTG CCT GTG AGG TCC 1120          1130          1140
AAG CTA GAG GAA GTC CAA AGA AAA CTT GGA 1150          1160          1170
TTT GCT CTT TCT GAC ATC TCG GTG GTT AGC 1180          1190          1200
AAT TAT TCC TCT GAG TGG GAG CTG GAC CCT
```

Fig. 1e

```
           1210              1220              1230
    GTA AAG GAT GTT CTA ATT CTT TCT GCT CTG 1240              1250              1260
    AGA CGA ATG CTA TGG GCT GCA GAT GAC TTC 1270              1280              1290
    TTA GAG GAT TTG CCT TTT GAG CAA ATA GGG 1300              1310              1320
    AAT CTA AGG GAG GAA ATT ATC AAC TGT GCA

1330
    CAA GGA AAA AAA 3'
                    5'
```

Fig. 2

AAAAATTTATTTGCTTTCAGGAAAATTTTTCTGT
TTTTTAAATAAACGAAAGTCCTTTTAAAAAGACA

ATAATGTGTGGAATTGTGAGCGGATAACAATTTC
TATTACACACCTTAACACTCGCCTATTGTTAAAG

Fig. 3a

```
          250             260             270             280             290             300
CTA GGA CTA TAT ACA CCA GAA ACA CTG TGT TGT GAC GTT GCA AAA TAT AAC TCC CCA
Leu Gly Leu Tyr Thr Pro Glu Thr Leu Phe Cys Asp Val Ala Lys Tyr Asn Ser Pro 310             320             330             340             350             360
ACT AAT TTC CAG ATA GAT GGA AGA AAT AGA AAA GTG ATT ATG GAC TTA AAG ACA ATG GAA
Thr Asn Phe Gln Ile Asp Gly Arg Asn Arg Lys Val Ile Met Asp Leu Lys Thr Met Glu 370             380             390             400             410             420
AAT CTT GCT CAA AAT TGT ACT ATC TCT ATT CAG GAT TAT GAA GTT TTT CGA TGC
Asn Leu Gly Leu Ala Gln Asn Cys Thr Ile Ser Ile Gln Asp Tyr Glu Val Phe Arg Cys 430             440             450             460             470             480
GAA GAT TCA CTG GAC GAA AGA ATA AAG GGG GTC ATT GAG CTC AGG AAG AGC TTA CTG
Glu Asp Ser Leu Asp Glu Arg Ile Lys Gly Val Ile Glu Leu Arg Lys Ser Leu Leu 490             500             510             520             530             540
TCT GCC TTG AGA ACT TAT GAA CCA TAT GGA TCC CTG GTT CAA CAA ATA CGA ATT CTG CTG
Ser Ala Leu Arg Thr Tyr Glu Pro Tyr Gly Ser Leu Val Gln Gln Ile Arg Ile Leu Leu 550             560             570             580             590             600
CTG GGT CCA ATT GGA GCT GGG AAG TCT AGC TTT TTC AAC TCA GTG AGG TCT GTT TTC CAA
Leu Gly Pro Ile Gly Ala Gly Lys Ser Ser Phe Phe Asn Ser Val Arg Ser Val Phe Gln
```

Fig. 3b

```
      610              620              630              640              650              660
GGG CAT GTA ACG CAT CAG GCT TTG GTG GGC ACT AAT ACA ACT GGG ATA TCT GAG AAG TAT
Gly His Val Thr His Gln Ala Leu Val Gly Thr Asn Thr Thr Gly Ile Ser Glu Lys Tyr 670              680              690              700              710              720
AGG ACA TAC TCT ATT AGA GAC GGG AAA GAT GGC AAA TAC CTG CCA TTT ATT CTG TGT GAC
Arg Thr Tyr Ser Ile Arg Asp Gly Lys Asp Gly Lys Tyr Leu Pro Phe Ile Leu Cys Asp 730              740              750              760              770              780
TCA CTG GGG CTG AGT GAG AAA GAA GGC GGC GGG CTG TGC ATG GAT GAC ATA TCC TAC ATC TTG
Ser Leu Gly Leu Ser Glu Lys Glu Gly Gly Leu Cys Met Asp Asp Ile Ser Tyr Ile Leu 790              800              810              820              830              840
AAC GGT AAC ATT CGT GAT AGA TAC CAG TTT AAT CCC ATG GAA TCA ATC AAA TTA AAT CAT
Asn Gly Asn Ile Arg Asp Arg Tyr Gln Phe Asn Pro Met Glu Ser Ile Lys Leu Asn His 850              860              870              880              890              900
CAT GAC TAC ATT GAT TCC CCA TCG CTG AAG GAC AGA ATT CAT TGT GTG GCA TTT GTA TTT
His Asp Tyr Ile Asp Ser Pro Ser Leu Lys Asp Arg Ile His Cys Val Ala Phe Val Phe 910              920              930              940              950              960
GAT GCC AGC TCT ATT GAA TAC TTC TCC CAG ATG ATA GTA AAG ATC AAA AGA ATT CGA
Asp Ala Ser Ser Ile Glu Tyr Phe Ser Gln Met Ile Val Lys Ile Lys Arg Ile Arg 970              980              990              1000             1010             1020
AGG GAG TTG GTA AAC GCT GGT GTA CAT GTT GCT TTG CTC ACT CAT GTG GAT AGC ATG
Arg Glu Leu Val Asn Ala Gly Val His Val Ala Leu Leu Thr His Val Asp Ser Met
```

Fig. 3c

```
     1030            1040            1050            1060            1070            1080
GAT CTG ATT ACA AAA GGT GAC CTT ATA GAA ATA GAG AGA TGT GTG CCT GTG AGG TCC AAG
Asp Leu Ile Thr Lys Gly Asp Leu Ile Glu Ile Glu Arg Cys Val Pro Val Arg Ser Lys 1090            1100            1110            1120            1130            1140
CTA GAG GTC CAA AGA AAA CTT GGA TTT GCT CTT TCT GAC ATC TCG GTG GTT AGC AAT
Leu Glu Val Gln Arg Lys Leu Gly Phe Ala Leu Ser Asp Ile Ser Val Val Ser Asn 1150            1160            1170            1180            1190            1200
TAT TCC TCT GAG TGG GAG CTG GAC CCT GTA AAG GAT GTT CTA ATT CTT TCT GCT CTG AGA
Tyr Ser Ser Glu Trp Glu Leu Asp Pro Val Lys Asp Val Leu Ile Leu Ser Ala Leu Arg 1210            1220            1230            1240            1250            1260
CGA ATG CTA TGG GCT GCA GAT GAC TTC TTA GAG GAT TTG CCT TTT GAG CAA ATA GGG AAT
Arg Met Leu Trp Ala Ala Asp Asp Phe Leu Glu Asp Leu Pro Phe Glu Gln Ile Gly Asn 1270            1280            1290            1300
CTA AGG GAG GAA ATT ATC AAC TGT GCA CAA GGA AAA AAA TAG ***
Leu Arg Glu Glu Ile Ile Asn Cys Ala Gln Gly Lys Lys ***
```

Fig. 4a

```
        10         20         30         40         50         60         70         80
5' GGGGGCTAC CCTCAGTCT AGCTCATACT ACAGACAGTA CAACAGATCA AGAAGTATGG CAGTGACAAC TCGTTTGACA
3' CCCCCCGATG GGAGTCGAGA TCGAGTATGA TGTCTGTCAT GTTGTCTAGT TCTTCATACC GTCACTGTTG AGCAAACTGT 90        100        110        120        130        140        150        160
   TGGTTGCATG AAAAGATCCT GCAAAATCAT TTTGGAGGGA AGCGGCTTAG CCTTCTCTAT AAGGGTAGTG TCCATGGATT
   ACCAACGTAC TTTTCTAGGA CGTTTTAGTA AAACCTCCCT TCGCCGAATC GGAAGAGATA TTCCCATCAC AGTACCTAA 170        180        190        200        210        220        230        240
   CCATAATGGA GTTTTGCTTG ACAGATGTTG TAATCAAGGG CCTACTCTAA CAGTGATTTA TAGTGAAGAT CATATTATTG
   GGTATTACCT CAAACGAAC TGTCTACAAC ATTAGTTCCC GGATGAGATT GTCACTAAAT ATCACTTCTA GTATAATAAC 250        260        270        280        290        300        310        320
   GAGCATATGC AGAAGAGGGT TACCAGGAAA GAAAGTATGC TTCCATCATC CTTTTTGCAC TTCAAGAGAC TAAAATTTCA
   CTCGTATACG TCTTCTCCCA ATGGTCCTTT CTTTCATACG AAGGTAGTAG GAAAAACGTG AAGTTCTCTG ATTTTAAAGT 330        340        350        360        370        380        390        400
   GAATGGAAAC TAGGACTATA TACACCAGAA ACACTGTTTT GTTGTGACGT TGCAAAATAT AACTCCCCAA CTAATTTCCA
   CTTACCTTTG ATCCTGATAT ATGTGGTCTT TGTGACAAAA CAACACTGCA ACGTTTTATA TTGAGGGGTT GATTAAAGT 410        420        430        440        450        460        470        480
   GATAGATGGA AGAAATAGAA AAGTGATTAT GGACTTAAAG ACAATGGAAA ATCTTGGACT TGCTCAAAAT TGTACTATCT
   CTATCTACCT TCTTTATCTT TTCACTAATA CCTGAATTTC TGTTACCTTT TAGAACCTGA ACGAGTTTTA ACATGATAGA 490        500        510        520        530        540        550        560
   CTATTCAGGA TTATGAAGTT TTTCGATGCG AAGATTCACT GGACGAAAAG AAGATAAAAG GGTCATTGA GCTCAGGAAG
   GATAAGTCCT AATACTTCAA AAAGCTACGC TTCTAAGTGA CCTGCTTTCT TTCTATTTC CCCAGTAACT CGAGTCCTTC
```

Fig. 4b

```
        570        580        590        600        610        620        630        640
AGCTTACTGT CTGCCTTGAG AACTTATGAA CCATATGGAT CCCTGGTTCA ACAAATACGA ATTCTGCTGC TGGGTCCAAT
TCGAATGACA GACGGAACTC TTGAATACTT GGTATACCTA GGGACCAAGT TGTTTATGCT TAAGACGACG ACCCAGGTTA 650        660        670        680        690        700        710        720
TGGAGCTGGG AAGTCTAGCT TTTTCAACTC AGTGAGGTCT GTTTTCCAAG GGCATGTAAC GCATCAGGCT TTGGTGGCA
ACCTCGACCC TTCAGATCGA AAAAGTTGAG TCACTCCAGA CAAAAGGTTC CCGTACATTG CGTAGTCCGA AACCACCGT 730        740        750        760        770        780        790        800
CTAATACAAC TGGGATATCT GAGAAGTATA GGACATACTC TATTAGAGAC GGGAAAGATG GCAAATACCT GCCATTTATT
GATTATGTTG ACCCTATAGA CTCTTCATAT CCTGTATGAG ATAATCTCTG CCCTTTCTAC CGTTTATGGA CGGTAAATAA 810        820        830        840        850        860        870        880
CTGTGTGACT CACTGGGGCT GAGTGAGAAA GAAGGCGGCC TGTGCATGGA TGACATATCC TACATCTTGA ACGGTAACAT
GACACACTGA GTGACCCCGA CTCACTCTTT CTTCCGCCGG ACACGTACCT ACTGTATAGG ATGTAGAACT TGCCATTGTA 890        900        910        920        930        940        950        960
TCGTGATAGA TACCAGTTTA ATCCCATGGA ATCAATCAAA TTAAATCATC ATGACTACAT TGATTCCCCA TCGCTGAAGG
AGCACTATCT ATGGTCAAAT TAGGGTACCT TAGTTAGTTT AATTTAGTAG TACTGATGTA ACTAAGGGGT AGCGACTTCC 970        980        990       1000       1010       1020       1030       1040
ACAGAATTCA TTGTGTGGCA TTTGTATTTG ATGCCAGCTC TATTGAATAC TTCTCCTCTC AGATGATAGT AAAGATCAAA
TGTCTTAAGT AACACACCGT AAACATAAAC TACGGTCGAG ATAACTTATG AAGAGGAGAG TCTACTATCA TTTCTAGTTT 1050       1060       1070       1080       1090       1100       1110       1120
AGAATTCGAA GGGAGTTGGT AAACGCTGGT GTGGTACATG TGGCTTTGCT CACTCATGTG GATAGCATGG ATCTGATTAC
TCTTAAGCTT CCCTCAACCA TTTGCGACCA CACCATGTAC ACCGAAACGA GTGAGTACAC CTATCGTACC TAGACTAATG
```

Fig. 4c

```
        1130       1140       1150       1160       1170       1180       1190       1200
AAAGGTGAC  CTTATAGAAA TAGAGAGATG TGTGCCTGTG AGGTCCAAGC TAGAGGAAGT CCAAAGAAAA CTTGGATTTG
TTTCCACTG  GAATATCTTT ATCTCTCTAC ACACGGACAC TCCAGGTTCG ATCTCCTTCA GGTTTCTTTT GAACCTAAAC 1210       1220       1230       1240       1250       1260       1270       1280
CTCTTTCTGA CATCTCGGTG GTTAGCAATT ATTCCTCTGA GTGGGAGCTG GACCCTGTAA AGGATGTTCT AATTCTTTCT
GAGAAAGACT GTAGAGCCAC CAATCGTTAA TAAGGAGACT CACCCTCGAC CTGGGACATT TCCTACAAGA TTAAGAAAGA 1290       1300       1310       1320       1330       1340       1350       1360
GCTCTGAGAC GAATGCTATG GGCTGCAGAT GACTTCTTAG AGGATTTGCC TTTTGAGCAA ATAGGGAATC TAAGGGAGGA
CGAGACTCTG CTTACGATAC CCGACGTCTA CTGAAGAATC TCCTAAACGG AAAACTCGTT TATCCCTTAG ATTCCCTCCT 1370       1380       1390       1400       1410       1420       1430       1440
AATTATCAAC TGTGCACAAG GAAAAAAATA GATATGTGAA AGGTTCACGT AAATTTCCTC ACATCACAGA AGATTAAAAT
TTAATAGTTG ACACGTGTTC CTTTTTTTAT CTATACACTT TCCAAGTGCA TTTAAAGGAG TGTAGTGTCT TCTAATTTTA 1450       1460       1470       1480       1490       1500       1510       1520
TCAGAAAGGA GAAAACACAG AGTAACTAAG ACCAAAGGGA TGTGTTTTAT TAATGTCTAG GATGAAGAAA
AGTCTTTCCT CTTTTGTGTC TCATTGATTC TGGTTTCCCT ACACAAAATA ATTACAGATC CTACTCTTT 1530       1540       1550       1560       1570       1580       1590       1600
TGCATAGAAC ATTGTAGTAC TTGTAAATAA CTAGAAATAA CATGATTAG CATGATTAG CAAAAATAAT AATAATTTTT
ACGTATCTTG TAACATCATG AACATTATT GATCTTTATT GTACTAAATC AGTATTAACA CTTTTTATTA TTATTAAAAA 1610       1620       1630       1640       1650       1660
CTTGGATTTA TGTTCTGTAT CTGTGAAAAA ATAAATTTCT TATAAAAAAA AAAAAAAA  3'
GAACCTAAAT ACAAGACATA GACACTTTTT TATTTAAAGA ATATTTTTT  TTTTTTTT  5'
```

DNA FRAGMENTS CODING FOR ANTIGENS SPECIFIC TO NON-A NON-B HEPATITIS, EXPRESSION VECTORS CONTAINING SAID DNA FRAGMENTS, TRANSFORMANTS AND PROCESS FOR PRODUCING SAID ANTIGENS

BACKGROUND OF THE INVENTION

1. Field of the Invention:

The present invention generally relates to the production of an antigen specific to non-A non-B hepatitis by recombinant DNA technology. More particularly, it relates to a DNA fragment coding for an antigen specifically occurring in a host affected with non-A non-B hepatitis, an expression vector containing such a DNA fragment, a host transformed with such an expression vector, as well as a process for producing said antigen specific to non-A non-B hepatitis by culturing such a transformant.

2. Description of the Prior Art:

Among viral hepatitises, the viral entities of hepatitis type A and type B have been found and, accordingly, it has now become possible to diagnose such diseases by immunological methods.

Still another type of hepatitis different from the types A and B, which is called non-A non-B type hepatitis, is said to be over 90% of post-transfusion hepatitis: refer to NIPPON RINSHO (Japan Clinic), 35, 2724 (1977): J. Biol. Med., 49, 243 (1976). The pathogenic virus of the non-A non-B type hepatitis, however, has not yet been identified. Only one fact which has already been established is potential infection of human hepatitis type non-A non-B virus to chimpanzee: refer to Lancet I, 459 (1978) ibid., 463 (1978).

Many workers have done various investigations for searching an antigen-antibody system related to the non-A non-B hepatitis by using mainly sera from patients affected with the disease; nevertheless, no definite system has been found. Under these circumstances, the diagnosis of non-A non-B hepatitis should inevitably be effected by so-called exclusion diagnosis: that is, whether or not the hepatitis of a patient is type A or type B or other hepatitis due to a virus known to cause hepatopathy, for example, CMV, HSV, EBV, etc., is first determined; and if not, the patient's hepatitis is diagnosed as non-A non-B type. Thus, such a diagnosis of non-A non-B hepatitis will require much time and labor.

An antigenic protein specific to non-A non-B hepatitis and useful for the direct diagnoses of the hepatitis has been purified from human and chimpanzee hepatocytes affected with non-A non-B hepatitis, and a monoclonal antibody specific to the antigen and useful for the treatment of the non-A non-B hepatitis has also been proposed: refer to Japanese Patent Application Laying-open (KOKAI) Nos. 176856/86 and 56196/86.

A large amount of such an antigenic protein specific to non-A non-B hepatitis should be required when such a protein is to be employed, for example, as a diagnostic agent. However, it is not always appropriate to purify such a large amount of the antigenic protein from chimpanzee hepatocytes affected with non-A non-B hepatitis.

On the other hand, in order to detect a gene coding for a specific antigen of non-A non-B hepatitis by nucleic acid hybridization and, further, to produce such an antigen specific to non-A non-B hepatitis by the recombinant DNA technology, it is essential to obtain a gene fragment coding for the antigenic protein specific to the non-A non-B hepatitis.

SUMMARY OF THE INVENTION

The present inventors have made great efforts to produce such a specific antigenic protein in a large amount by genetic engineering techniques, and finally isolated a gene fragment coding for the antigenic protein specific to non-A non-B hepatitis, said gene fragment being useful for the production of such antigens. Furtner, the inventors have successfully constructed an expression vector containing said gene fragment. Thus, the present invention has now been attained.

It is an object of the invention to provide a DNA fragment which contains a base sequence coding for an antigen specifically occurring in a host cell affected with non-A non-B hepatitis or an antigenic protein specific to non-A non-B hepatitis having physiological activities equivalent to those of said specifically occurring antigen.

Another object of the invention is to provide an expression vector having said DNA fragment introduced thereinto at a cloning site downstream from a promoter of the vector.

A still another object of the invention is to provide a transformant obtained by transforming a host cell with said expression vector.

A further object of the invention is to provide a process for producing such an antigen specific to non-A non-B hepatitis by culturing said transformant.

BRIEF DESCRIPTION OF THE DRAWINGS

Other objects and advantages of the present invention will be apparent from the following detailed description with reference to the attached drawing, in which:

FIGS. 1a–1e show the base sequence coding for an antigenic protein specific to non-A non-B hepatitis;

FIG. 2 shows the base sequence of a hybrid promoter Pac;

FIGS. 3a–3c show the base sequence of a cDNA fragment obtained in Example 1 described hereinbelow, together with deduced amino acid sequence;

FIGS. 4a–4c show the base sequence of cDNA containing the full length gene sequence of an antigenic protein specific to non-A non-B hepatitis, which cDNA was obtained in Example 2 described hereinbelow, the base sequence 57-1388 thereof coding for the antigenic protein specific to non-A non-B hepatitis;

DETAILED DESCRIPTION OF THE INVENTION

Figure 5:
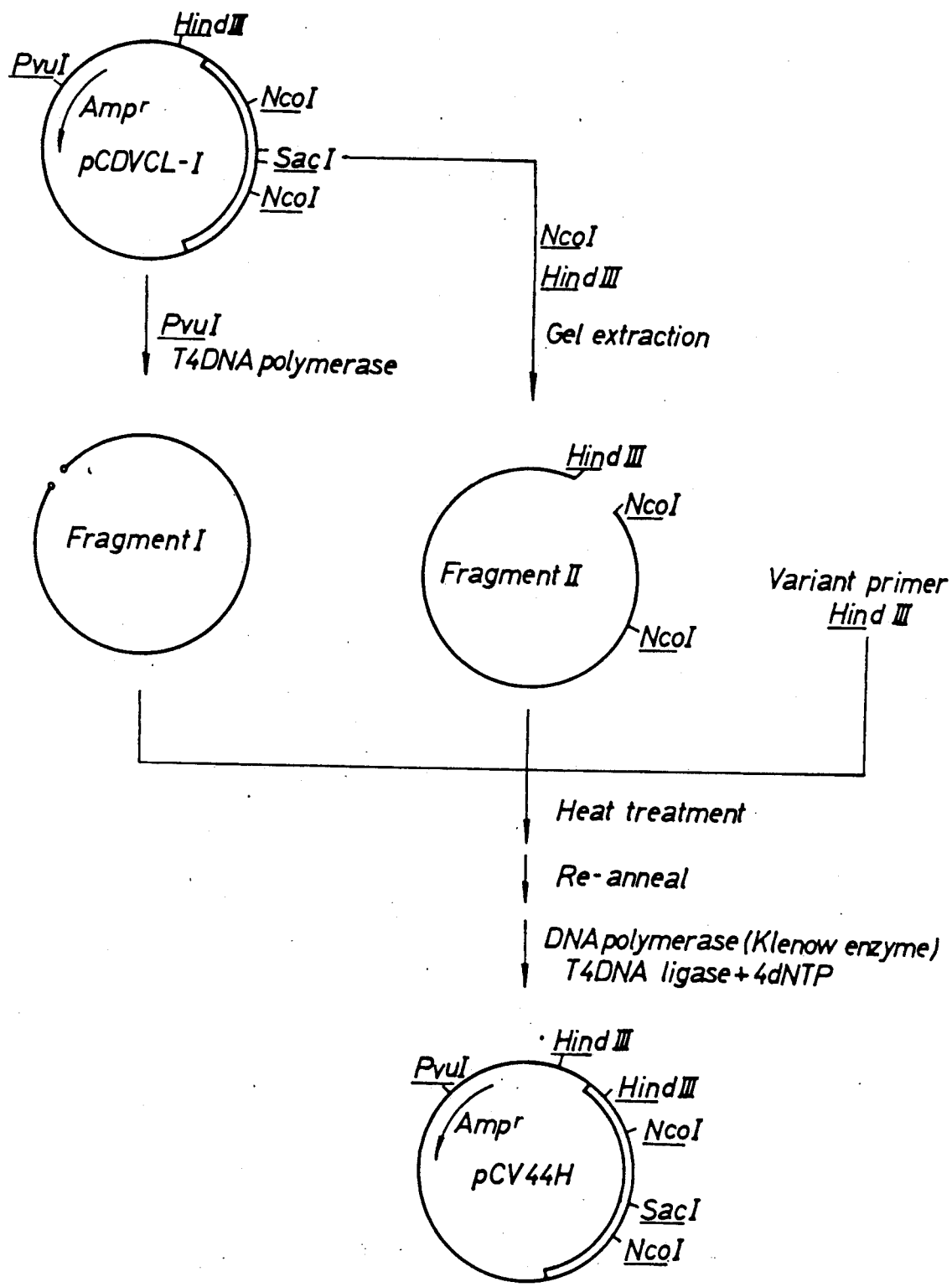
FIG. 5 schematically illustrates the construction of a plasmid pCV44H.

The present invention will be described in detail hereinbelow.

According to one aspect of the invention, a DNA fragment is provided which contains a base sequence coding for an antigenic protein occurring specifically in hepatocytes affected with non-A non-B hepatitis.

Such a DNA fragment of the invention may be prepared in the following manner.

First, a liver tissue specimen derived from a human or chimpanzee individual affected with non-A non-B hepatitis is homogenized in an aqueous solution of guanidinium thiocyanate and then subjected to cesium chloride equilibrium dnsity gradient centrifugation according to Chirgwin et al. method (Biochemistry, 18, 5294-5299 (1979)) to separate total RNA as a precipitate. After separation, the total RNA is purified by phenol extraction and ethanol precipitation.

"Individuals affected with non-A non-B hepatitis" used as sources of liver tissue specimens in the invention may include those affected with so-called type D hepatitis, which has recently been named.

It is known that mRNA of an antigen gene generally has a poly-A chain. Thus, the total RNA is subjected to oligo(dT) cellulose column chromatography in a conventional manner and poly(A)-containing RNA (poly AA+ RNA) is isolated as mRNA material.

A cDNA library corresponding to the poly A+ RNA is then obtained from the mRNA material according to the random primer method (Y. Ebina et al., Cell, 40, 747-758 (1980)): Thus, a number of DNAs complementary to the mRNA material are randomly synthesized using any primer of e.g. about 6 bases and a reverse transcriptase.

The cDNA is methylated with a DNA methylase, e.g. EcoRI methylase, to protect cleavage sites present in the cDNA capable of being cleaved by a corresponding restriction enzyme, e.g. EcoRI. A DNA linker containing the corresponding restriction enzyme cleavage sites at both ends, e.g. EcoRI linker (CGAATTCG), is added to the methylated cDNA and, then, this cDNA is digested with the restriction enzyme, e.g. EcoRI.

The digested cDNA is then cloned into a cloning vector such as a plasmid or a λ phage. For example, the cDNA may be introduced into EcoRI site of λgt 11 DNA, which is an expression cloning vector: refer to R. A. Young et al., Pro. Natl. Acad. Sci. U.S.A., 80, 1194-1198 (1983). The cDNA will be inserted into the β-gal gene on the λgt 11 phage. Thus, expression of the cDNA can be easily verified by the production of a fused protein with β-galactosidase due to induction of the expression by the lactose operon promoter of said phage when E. coli transfected with said phage is cultured in a medium containing IPTG (isopropylthio-β-D-galactopyranoside).

The λgt 11 phage incorporating the cDNA is then introduced into E. coli by Tomizawa et al. method in "Experimental Procedures for Bacteriophages", pp. 99-174, published May 30, 1970 by Iwanami Shoten (Japan). The thus transfected microorganism is cultured in an IPTG-containing medium.

The thus formed plaques can be easily selected by an immunological screening method using a monoclonal antibody specifically directed to non-A non--B hepatitis to obtain a desired cDNA. Such a monoclonal antibody which can be used in the immunological screening method may be prepared according to the methods described in Japanese Patent Application Laying-open Nos. 176856/86 and 56196/86. The screening methods used may include the western blotting technique described in these applications.

The plaques positive in the immunological screening test are selected to proliferate the phage by Tomizawa et al. method. DNA is purified from the grown phage by T. Maniatis et al. method in "Molecular Cloning", Cold Spring Harbor Laboratory, pp. 85 et seq. (1982), and cleaved with a suitable restriction enzyme such as EcoRI. The thus purified and digested DNA fragments can be used to determine the base sequence of a desired cDNA segment according to Maxam and Gilbert method in Methods in Enzymology, 65, 499-560 (1980); or alternatively, after further cloning the DNA fragments into M13 phage, the base sequence of such a desired cDNA segment can be determined according to the dideoxy method: Sanger et al., Proc. Natl. Acad. Sci. U.S.A., 74, 5463 (1977).

Thus, a cDNA fragment coding for an antigen specific to non-A non-B hepatitis can be obtained. However, such a DNA fragment may usually be only a portion of the gene coding for the non-A non-B hepatitis-specific antigen.

A full length cDNA coding for such a non-A non-B hepatitis-specific antigen may be obtained in the following manner.

Poly A+-mRNA is isolated and purified in a manner similar to that described above. From the poly A+-mRNA a cDNA library is obtained according to Okayama-Berg vectorprimer method: Molecular and Cellular Biology, 2, 161-170 (1982).

A plasmid containing such a cDNA thus prepared is used to transform E. coli by any conventional method, for instance, the method D. Hanahan: J. Mol. Biol., 166, 557 (1983). The transformant ampicillin-resistant strains are collected and screened by the colony hybridization method using the aforementioned DNA fragment as a probe. Such a probe may preferably be prepared by either the strepto-avidin method, or the nick translation method using photobiotinnucleic acids and $^{32}P$-nucleic acids The thus selected colonies containing a cDNA clone are cultured. Plasmid DNA is obtained t rom the cultured colony according to Birmboim et al. method (Nucleic Acid Res., 7, 1513 (1979)) and digested with a suitable restriction enzyme. The base sequence of a desired full-length cDNA segment is then determined according to the aforementioned Maxam and Gilbert method or, alternatively, after further cloning the digested DNA into M13 phage or pVC12 plasmid, such a base sequence is determined according to the above described Sanger et al. dideoxy method.

The base sequence of the full ength DNA coding for an antigen specific to non-A non-B hepatitis is shown in FIG. 1, in which the symbol "—" just under the base sequence represents a corresponding base complementary to the respective base described just above each of the symbols.

Of course, DNA fragments which can be employed in the invention do not necessarily contain the same base sequence as shown in FIG. 1, but those DNA fragments in which a part of said base sequence shown in FIG. 1 has been substituted by at least one different base or deleted therefrom and those DNA fragments in which one or more additional bases have been added to the base sequence of FIG. 1 may also be included herein provided that such different DNA fragments may code for substances having physiological activities equivalent to those of the non-A non-B hepatitis-specific antigens encoded by the base sequence of FIG. 1.

According to another aspect or the invention, an expression vector is provided in which the aforementioned DNA fragment of the invention is inserted into a cloning site downstream from a promoter of this vector.

The expression vector of the invention contains a promoter in a position capable of controlling the transcription of a DNA fragment coding for a non-A non-B hepatitis-specific antigen obtained by the aforementioned method. The promoters used in the invention may be any promoter capable of expressing the DNA fragment in a host, and preferably of controlling the transcription of the fragment.

When a host used is a microorganism such as *Escherichia coli, Bacillus subtilis,* etc., the expression vector of the invention may preferably comprise a promoter, a ribosome binding sequence, a gene for a non-A non-B hepatitis-specific antigen, a transcription termination factor, and a gene controlling the promoter.

The promoter used may include those derived from *E. coli,* phage, etc., for example, tryptophan synthase operon (trp), lactose operon (lac), lipoprotein (lpp), recA, lambda phage $P_L$, $P_R$, T5 early gene $P_{25}$, $P_{26}$ promoter, which may also be prepared by chemical synthesis. Also included herein are hybrid promoters such as tac (trp:lac), trc (trp:lac) and Pac (phage: *E. coli* ) shown in FIG. 2.

The ribosome binding sequence may be derived from *E. coli,* phage, etc., but preferably may be those synthetically prepared, for example, those containing a consensus sequence such as AGGAGGTTTAA.
SD sequence The gene for a non-A non-B hepatitis-specific antigen may be directly employed without any modification. Preferably, an unnecessary base sequence (non-coding region) may be deleted by site-directed mutagenesis: BIO TECHNOLOGY, July, 636–639 (1984).

A transcription termination factor may not always be required in the expression vector of the invention. Preferably, the instant vector may contain a ρ-independent terminator, for example, lpp terminator, trp operon terminator, ribosomal RNA gene terminator, etc.

The expression vector may be derived from any conventional plasmid. Preferably, it may be derived from such a plasmid as replicating itself in *E. coli* or *Bacillus subtilis,* for example, pBR322- or pUB110-derived plasmid.

Desirably, these factors required for expression are arranged in the expression plasmid in the order of the promoter, the SD sequence, the structural gene of a non-A non-B hepatitis-specific antigen, and the transcription termination factor from 5' to 3'. A repressor gene required to control the transcription, a marker gene such as drugresistant gene, and a plasmid replication origin may be arranged in any order in the expression vector.

The expression vector of the invention may be introduced into a host by any conventional method for transformation of *E. coli,* e.g., one described in Molecular Cloning, 250–253 (1982), or of *Bacillus subtilis,* e.g., one described in Molec. Gen. Genet., 168, 111–115 (1979) or Proc. Nat. Acad. Sci. U.S.A., 44, 1072–1078 (1958).

The resulting transformant may be cultured in any conventional medium, e.g. one described in Molecular Cloning, 68–73, (1972), at a temperature in the range of 28° to 42° C. in both cases of *E. coli* and *Bacillus subtilis.* Preferably, it may be cultured at a temperature in the range of 28° to 30° C. where no expression of heat shock proteins may be induced.

The desired protein thus produced may be easily purified from the host in conventional procedures. For example, the host cell may be crushed by lysozyme-surfactant or ultrasonication, and the insoluble fractions which contain the desired non-A non-B hepatitis-specific antigen may be then collected by centrifugation, solubilized in a surfactant such as 0.01% SDS, and subjected to column chromatography using a monoclonal antibody (Japanese Patent Application Laying-open (KOKAI) Nos. 56196/86 and 176856/86.

When an eukaryotic cell such as an animal cell is employed as a host, the expression vector of the invention is preferably as follows:

The promoters used in the vector of the invention for the expression in eukaryotic cells may herein include SV40 early and late promoters; promoters of apolipoprotein E and A-I genes; promoter of heat shock protein gene (Proc. Natl. Acad. Sci. U.S.A., 78, 7038–7042 (1981)); promoter of metallothionein gene (Proc. Natl. Acad. Sci. U.S.A., 77, 6511–6515 (1980)); HSV TK promoter; adenovirus promoter, such as Ad2 major late promoter (Ad2 MLP); LTR (long terminal repeat) of retrovirus; etc. SV40 promoter and promoter of metallothionein gene are preferred.

The expression vector of the invention may contain a splice sequence comprising 5' splice junction donor site, an intron and 3' splice junction acceptor site. A common base sequence is found at all the splice junction sites (exonintron junction sites); so-called GT/AG rule that any intron region always starts from two bases GT at the donor site and terminates at two bases AG of the acceptor site has been established.

The expression vector of the invention may contain one or more splice sequences as mentioned just above. Such splice sequences may be positioned upstream or downstream of the structural gene for a non-A non-B hepatitis-specific antigen.

Illustrative examples of such splice sequences may include those DNA sequences found in exons 2 and 3 of rabbit β-globin gene (Science, 26, 339 (1979)) and mouse methallothionein-I gene containing the promoter, exons 1, 2 and 3 and introns A and B of methallothionein gene (Proc. Natl. Acad. Sci. U.S.A., 77, 6513 (1980)). The 5' and 3' splice sites may be derived from the same or different gene; for example, a sequence in which 5' splice site contained in adenovirus DNA is linked to 3' splice site derived from the gene of Ig variable region can be employed.

The expression vector of the invention also contains a polyadenylation site downstream from the structural gene of a non-A non-B hepatitis-specific antigen. Illustrative examples of the polyadenylation sites may include those derived from SV40 DNA, β-globin gene or methallothionein gene. A combined site of the polyadenylation sites of β-globin gene and SV40 DNA may be employed in the invention.

The expression vector of the invention may also contain a dominant selective marker permitting the selection of transformants. Selective markers which can be used herein may include DHFR gene imparting MTX (methotrexate) resistance to a host; tk gene of herpes simplex virus (HSV) which permits selection of tk⁻ strains transformed therewith in HAT medium; the gene for aminoglycoside 3'-phosphotransferase from *E. coli* transposon Tn5, which imparts to a host the resistance against 3'-deoxystreptamine antibiotic G418; bovine papilloma virus gene permitting morphological discrimination by piled up growth; and aprt gene.

Alternatively, animal cells transformed with the expression vector of the invention may be selected by the cotransformation even though no selective marker is present in the vector. For this purpose, an animal cell is cotransformed with both the expression vector and a plasmid or other DNA containing a gene for such a selective marker and selected by a phenotypic trait of the gene.

Advantageously, the expression vectors may also contain a plasmid fragment having an origin of replication derived from a bacterium such as E. coli, since such vectors can be cloned in bacteria. Such plasmids may include pBR322, pBR327, pML, etc.

Illustrative examples of plasmid vectors used as sources of the expression vectors according to the invention may include pKCR (Proc. Natl. Acad. Sci. U.S.A., 78, 1528 (1981)), which contains SV40 early promoter, the splice sequence and polyadenylation site derived from rabbit β-globin gene, the polyadenylation site from SV40 early region, and the origin of replication and ampicillin resistant gene from pBR322; pKCR H2 (Nature, 307, 605 (1984)), in which the pBR322 portion of pKCR has been substituted by pBR327 fragment and the EcoRI site present in the exon 3 of rabbit β-globin gene has been converted into HindIII site; and pBPV MT1 containing BPV gene and methallothionein gene (Proc. Natl. Acad. Sci. U.S.A., 80, 398 (1983)).

Animal cells transformed with the expression vector of the invention may include CHO cells, COS cells, and mouse L cells, C127 cells and FM3A cells.

The introduction of the expression vector of the invention into an animal cell may be carried out by transfection, microinjection, etc. Most often, the transfection may employ $CaPO_4$: Virology, 52, 456–467 (1973).

Animal cells transformed by introducing the expression vector of the invention may be cultured in a suspension or solid medium by conventional methods. The culture medium used is most often MEM, RPMI1640, etc.

Proteins produced in the transformed animal cells can be separated and purified in the almost same manner as in the case of microorganisms aforementioned.

As stated, the invention provides a transformant cell obtained by introducing the expression vector of the invention into a host cell.

Also provided according to the invention is a process for producing a non-A non-B hepatitis-specific antigen comprising culturing said transformant and collecting the produced and accumulated antigen.

As stated previously, a large amount of an antigenic protein specific to non-A non-B hepatitis is required when such a protein is to be utilized as a direct diagnostic agent. According to the present invention, such an antigenic protein can be produced with a low cost and a large scale without use of infected chimpanzee hepatocytes. Prior to the present invention, it has been difficult obtain such a large amount of a non-A non-B hepatitis-specific antigenic protein from hepatocytes of chimpanzees affected with non-A non-B hepatitis.

Further, the DNA fragment coding for an antigenic protein of non-A non-B hepatitis virus according to the present invention will be useful as a probe for detecting the gene of said antigenic protein by nucleic acid hybridization.

EXAMPLES

The following examples will be given by way of illustration but these examples in no way limit the scope of the invention without departing the concept thereof.

EXAMPLE 1

Preparation of cDNA Fragment Coding for Antigenic Protein Specific to Non-A Non-B Hepatitis Poly(A)-containing RNA was prepared from chimpanzee liver according to the guanidine thiocyanate-lithium chloride method: Cathala et al., DNA, 2, 329 (1983).

The infected liver (5 g) was taken out from a chimpanzee affected with non-A non-B hepatitis and immediately frozen by liquid nitrogen. The frozen liver was added into a Waring blender together with liquid nitrogen and ground at 3,000 rpm for 2 minutes. The ground liver specimen was further ground by a Teflon homogenizer at 5 rpm in 100 ml of a solution: 5 M guanidine thiocyanate, 10 mM EDTA, 50 mM Tris-HCl (pH 7), 8% (v/v) β-mercaptoethanol. The thus solubilized material (20 ml) was slowly placed on 5.7 M CsCl solution (10 ml) contained in a centrifuge tube and centrifuged at 27,000 rpm for 20 hours in Hitachi RPS 28-2 rotor. The thus precipitated RNA was collected and dissolved in 10 ml of a solution: 0.1% sodium laurylsulfate, 1 mM EDTA, 10 mM Tris-HCl (pH 7.5). The RNA was extracted with phenol-chloroform and recovered by ethanol precipitation.

The thus obtained RNA (about 3.95 mg) was dissolved in 1 ml of a solution: 10 mM Tris-HCl (pH B.0). 1 mM EDTA. The solution was incubated at 65° C. for 5 minutes, and 5M NaCl (0.1 ml) was added. The resulting mixture was subjected to chromatography on an oligo(dT) cellulose column (column volume of 0.5 ml, P-L Biochemical). The thus adsorbed poly(A)-containing mRNA was eluted with a solution: 10 mM Tris-HCl (pH 7.5), 1 mM EDTA. There was obtained about 100 μg of poly(A)-containing mRNA.

The thus obtained poly(A)+ mRNA (10 μg) was dissolved in 50 μl of RT buffer: 20 mM Tris-HCl (pH 8.8), 0.1M KCl, 12 mM $MgCl_2$, 2 mM $MnCl_2$. To this solution, there was added 8 μg of random primer $d(N)_6$ (P-L Biochemical). The resulting mixture was heated at 95° C. for 3 minutes to denature the materials, which was then cooled gradually to room temperature to anneal the random primer with the mRNA. To the annealed mixture, there were aded 10 mM 4NTP (10 μl) and reverse transcriptase (225 units) from TAKARA SHUZO (Japan), and then water was added so as to make the total volume of the mixture to 100 μl. Reaction was allowed to proceed at 42° C. for one hour.

To the reaction mixture (50 μl), there were added 10 mM NAD (2 μl), 10 mM 4dNTP (10 μl), RNase H (5 units), E. coli ligase (1 unit), E. coli DNA polymerase I (6.3 units), and 10x T4 DNA ligase buffer (10 μl; 0.1M Tris-HCl, pH 7.5, 0.1 M DTT, 60 mM $MgCl_2$) to make the total volume to 100 μl. The mixture was allowed to react at 37° C. for one hour to synthesize a double stranded DNA.

The thus obtained double stranded DNA was extracted with an equal volume of water-saturated phenol. Phenol in the aqueous layer was removed with the aid of ether followed by ethanol precipitation. The precipitate thus obtained was dissolved in 50 μl of water, and 10× T4 DNA polymerase buffer (10 μl; 0.33M Tris-acetic acid, pH 7.9, 0.66M potassium acetate, 0.1M magnesium acetate, 5 mM DTT), 10 mM 4dNTP (10 μl), and T4 DNA polymerase (6 units) were added to make the 1 total volume to 100 pl. The mixture was reacted at 37° C. for one hour. There was obtained a double stranded DNA having blunt ends, which was then extracted with phenol to remove proteins and purified by ethanol precipitation as described above. The thus purified DNA was then air dried.

To the purified DNA, there were added 50 mM Tris-HCl (pH 7.5), 1 mM Na$_2$EDTA, 5 mM DTT (20 µl), 100 µM S-adenosyl-L-methionine (2 µl), and 1.8 mg/ml EcoRI methylase (0.2 µl). Reaction was effected at 37° C. for 15 minutes, whereby methylating the EcoRI restriction enzyme cleavage site on the DNA fragment. The reaction mixture was then heated at 70° C. for 15 minutes to deactivate the enzyme.

To the reaction mixture, there was added 3'-phosphorylated EcoRI linker (GGAATTCC) in an amount of 100 molecules thereof per molecule of the synthetic DNA. There were further added 10× T4 DNA ligase buffer (5 µl; 0.5M Tris-HCl, pH 7.5, 60 mM MgCl$_2$, 10 mM DTT), 0.1M ATP (5 µl), and T4 DNA ligase (5 units) to make the total volume to 50 µl. The resulting reaction mixture was reacted at 4° C. for 16 hours followed by heating at 70° C. for 10 minutes to deactivate the 7.5, 0.5M NaCl, 60 mM MgCl$_2$), and EcoRI (100 units) were added to make the total volume to 100 µl, and the reaction mixture was reacted at 37° C. for 2 hours to cut the linker. The reaction mixture was passed through Bio Gel A-50 (0.2 cm ×32 cm, Bio RAD). Elution was effected by a buffer: 10 mM Tris-HCl (pH, 7.5), 6 mM MgCl$_2$. Excess EcoRI linker was removed and, thus, a double stranded cDNA having EcoRI sites at both ends thereof was purified.

To the thus obtained double stranded cDNA fragment having EcoRI sites at both ends, there were added λgt 11 DNA (10 µg) cleaved with EcoRI, 10× T4 DNA ligase buffer (10 µl) as described above, 0.1 M ATP (10 µl), and T4 DNA ligase (10 units) to make the total volume to 100 µl. The mixture was reacted at 4° C. for 16 hours. Thus, said double stranded cDNA fragment was inserted into λgt 11 DNA.

The λ phage packaging kit (PROMEGA, Biotech) was used to introduce said DNA into λ phage particle. The procedures for packaging were effected according to the instructions of the kit.

The λgt 11 phage having said DNA packaged thereinto was used to transfect E. coli strain Y1090 to form plaques according to the conventional Tomizawa et al. methods described in "Experimental Procedures for Bacteriophages", pp. 99-174, published May 30, 1970 by Iwanami Shoten (Japan). Among about 200,000 plaques, one positive clone was selected by immunological screening as described hereinbelow. A monoclonal antibody used in the immunological screening was prepared by the method described in Japanese Patent Application Laying-open (KOKAI) No. 176856/86.

E. coli Y1090 (R.A. Young et al., Pro. Natl. Acad. Sci. U.S.A., 80, 1194-1198 (1983), which had been transfected with λgt 11, was inoculated in a petri dish together with soft agar held at 42° C. The transfected cell was allowed to stand at 42° C. for 5 hours. A nitrocellulose filter (S & S, BA-83, pore size of 0.2 µm) containing 10 mM IPTG was placed on the cell in the dish and incubation was effected at 37° C. for 3-4 hours. This nitrocellulose filter was lightly rinsed with TBS buffer (10 mM Tris-HCl, pH 7.5, 50 mM NaCl), immersed in the TBS buffer (400 ml) containing 3% gelatine and shaked at 40° C. for one hour. Thus, the nitrocellulose filter was blocked. Then, a monoclonal antibody OD$_{280}$=4.3) directed to a non-A non-B hepatitis-specific antigen was added to TBS buffer containing 1% gelatine with a dilution of 1/400. This mixture was put into a vinyl bag together with the filter in a proportion of 2 ml of the mixture per filter, and reaction was allowed to proceed at room temperature for 16 hours. The reaction mixture was three times washed with TBS buffer (400 ml) containing 0.05% Tween 20 over 10 minutes. A labelled secondary antibody, anti-mouse IgG-PAP (horseradish peroxidase, Bio Rad) was added to TBS buffer containing 1% gelatine with a dilution of 1/1,000. This mixture and the filter were put into a vinyl bag with a proportion of 2 ml of the mixture per filter. Reaction was allowed to proceed at room temperature for 2 hours. The reaction mixture was three times washed with TBS buffer (400 ml) containing 0.05% Tween 20 over 10 minutes, in the same manner as described above. Color development was effected by dipping the filter and 4-chloro-1-naphthol (12 mg, Bio Rad) into 20 ml of TBS buffer containing hydrogen peroxide. After completion of the color development, the filter was thoroughly washed with water and put into a vinyl bag containing water. The bag was stored in a dark and cold place.

Thus, one positive plaque was obtained. The plaque was three times subjected to single plaque isolation. In each time, immunological screening was effected in the same manner as described above, verifying that the plaque was in fact positive.

The phage was then cultured in a large scale to purify the DNA in the following manner: First, E. coli Y1090 was cultured overnight in 10 ml of NZ medium prepared by adding NZ amine (10 g), NaCl (5 g) and 5 mM MgCl$_2$ to one liter of water followed by adjusting the pH to 7.2. The culture (1 ml) was transfected with the phage, with the m.o.i. (multiplicity of infection) being 0.1. The transfected culture was allowed to stand at 37° C. for 10 minutes and then transferred to one liter of NZ medium. Shaking culture was effected at 37° C. for 7-8 hours until the cells were lysed. Chloroform (5 ml) was added to the culture and shaking was continued for additional 30 minutes. The culture was subjected to centrifugation at 6,500 rpm for 10 minutes to remove cell debris.

NaCl (29 g) and polyethylene glycol (70 g) were added to and thoroughly dissolved in the obtained supernatant, and the solution was allowed to stand at 4° C. overnight. The precipitate was collected by centrifugation at 6,500 rpm for 20 minutes, drained thoroughly, and dissolved in 20 ml of TM buffer: 10 mM Tris-HCl (pH 7.5), 5 mM MgCl$_2$ DNase I and RNase A were added to the solution, both with a concentration of 10 µg/ml, and the reaction was effected at 37° C. for one hour. Chloroform (20 ml) was then added to the reaction mixture and stirred; thus, polyethylene glycol was distributed in the chloroform layer which was then separated from the aqueous layer. This aqueous layer was ultracentrifuged at 28,000 rpm for 60 minutes. Thus, a pellet of phage particles was obtained.

This pellet was dissolved in TM buffer (1 ml) and subjected to CsCl density gradient centrifugation at 33,000 rpm for 20 hours. The resultant fraction containing the phage particles ($\rho$=1.45-1.50) was dialyzed overnight against TM buffer. Proteinase K was added to the dialyzate in an amount of 100 µg/ml and reaction was effected at 37° C. for one hour. Thereafter, an equal volume of water-saturated phenol was added and phenol-extraction was gently effected. After centrifugation at 6,500 rpm for 10 minutes, the aqueous layer was removed, put into a dialysis tube, and dialyzed overnight against water at 4° C. Thus, about 5 mg of DNA was obtained.

Cleavage reaction of this DNA (100 µg) with EcoRI (100 units) in the aforementioned buffer (100 µl) at 37°

C. revealed that two cDNA segments of 390 bp and 345 bp were inserted into the phage DNA.

These two EcoRI fragments were re-cloned into EcoRI site of a cloning vector pUC 119. Base sequences of these DNA fragments were determined by the dideoxy method using commercially available primers CAGGAAACAGCTATGAC and AGTCAC-GACGTTGTA, respectively. The base sequence of the linking portion between these two DNA fragments was similarly determined by cutting this cDNA fragment at BamHI and EcoRV sites present therein with corresponding specific restriction enzymes, inserting the resulting BamHI-EcoRV DNA fragment between BamHI and SmaI sites of the plasmid pUC 119. and sequencing the fragment by the dideoxy method.

The base sequence of said cDNA fragment is shown in FIG. 3. This was a partial cDNA fragment of a gene coding for an antigenic protein specific to non-A non-B hepatitis.

EXAMPLE 2

Preparation of cDNA Containing the Full Length Gene Sequence

Messenger RNA was prepared as described in Example 1 and cDNA was synthesized using Okayama vector according to the conventional method described in Molecular Cloning, p. 211 et seq. The procedures used to synthesize cDNA were as follows:

To 300 µl of a solution (10 mM Tris-HCl, pH 7.5, 6 mM MgCl$_2$, 10 mM NaCl), there were added 400 µg of pCDV 1 (Okayama and Berg, Mol. Cell. Biol., 3, 280 (1983)) and 500 units of KpnI (TAKARA SHUZO, Japan), all restriction enzymes used hereinafter having been manufactured by TAKARA SHUZO (Japan) unless otherwise noted. Reaction was effected at 37° C. for 6 hours to cut the plasmid at KpnI site therein. After phenol-chloroform extraction, ethanol precipitation was effected to recover DNA.

The DNA (about 200 µg) cleaved with KpnI was added to 200 µl of a solution which was obtained by adding dTTP in a concentration of 0.25 mM to a buffer (TdT buffer): 40 mM sodium cacodylate 30 mM Tris-HCl (pH 6.8), 1 mM CaCl$_2$, 0.1 mM dithiothreitol (DTT). Further, 81 units of terminal deoxynucleotidyl transferase (TdT, manufactured by P-L Biochemicals) was also added. Reaction was effected at 37° C. for 11 minutes. Thus, a poly(dT) chain (about 67 deoxythymidylic acid residues) was added to the 3' end at the KpnI-cleaved site of pCDV 1. After phenol-chloroform extraction and ethanol-precipitation, about 100 µg of pCDV 1 DNA to which poly(dT) chain had been added was recovered from the reaction mixture.

The thus obtained DNA was added to 150 µl of a buffer (10 mM Tris-HCl, pH 7.5, 6 mM MgCl$_2$, 100 mM NaCl), and HpaI (360 units) was also added, followed by reaction at 37° C. for 2 hours. The reaction mixture was subjected to electrophoresis on agarose gel to separate and recover about 3.1 Kbp DNA fragment. Thus, there was obtained about 60 µg of poly(dT)-containing pCDV 1.

The thus obtained DNA was dissolved in 500 µl of a solution (10 mM Tris-HCl, pH 8.0, 1 mM EDTA), incubated at 65° C. for 5 minutes, and cooled on ice. After adding 5 M NaCl (50 µl), the mixture was subjected to chromatography on oligo(dA) cellulose column (Colaborative Research). DNA having a poly(dt) chain of sufficient length was adsorbed on the column and eluted with a solution, 10 mM Tris-HCl (pH 8.0), 1 mM EDTA. Thus, there was obtained 27 pg of pCDV 1 to which poly(dT) chain had been added, abbreviated hereinafter as vector primer.

A linker DNA was prepared in the following manner: To 200 µl of a solution (10 mM Tris-HCl, pH 7.5, 6 mM MgCl$_2$, 50 mM NaCl), there were added about 14 µg of pL 1 (Okayama and Berg, Mol. Cell. Biol., 3, 280 (1983)) and 50 units of PstI. Reaction was effected at 37° C. for 4 hours to cut the pL 1 DNA at PstI site. Phenol-chloroform extraction and ethanol precipitation of the reaction product gave about 13 µg of pL 1 DNA cleaved at PstI site.

The thus obtained DNA (about 13 µg) was added to 50 µl of the TdT buffer containing dGTP at a final concentration of 0.25 mM, and 54 units of TdT (P-L Biochemicals) was also added. The mixture was incubated at 37° C. for 13 minutes to add a (dG) chain (about 14 deoxyguanylic acid residues) to the 3' end at the PstI-cleaved site of pL 1. After phenol-chloroform extraction, DNA was recovered by ethanol precipitation.

The thus obtained DNA was added to 100 µl of a buffer (10 mM Tris-HCl, pH 7.5, 6 mM MgCl$_2$, 60 mM NaCl), and 80 units of HindIII was also added. The mixture was incubated at 37° C. for 3 hours to cut the pL 1 DNA at HindIII site. The reaction product was fractionated by agarose gel electrophoresis. About 0.5 Kb DNA fragment was recovered by the DEAE paper method: Dretzen et al., Anal. Biochem., 112, 295 (1981). Thus, there was obtained an oligo(dG) chain-containing linker DNA, hereinafter abbreviated simply as linker DNA.

The aforementioned poly(A)A+ RNA (about 2 µg) prepared in the same manner as in Example 1 and the vector primer (about 1.4 µg) were dissolved in 22.3 µl of a solution: 50 mM TrisHCl (pH 8.3), 8 mM MgCl , 30 mM KCl, 0.3 mM DTT, 2 mM dNTP (dATP, dTTP, dGTP and dCTP) and 10 units of ribonuclease inhibitor (P-L Biochemicals). To the solution, there was added 10 units of reverse transcriptase manufactured by SEIKAGAKU KOGYO (Japan). Incubation was effected at 37° C. for 40 minutes to synthesize a DNA complementary to the mRNA. After phenol-chloroform extraction and ethanol precipitation, the vector primer DNA to which a double stranded RNA-DNA had been added was recovered.

The thus obtained vector primer DNA containing RNA-DNA double stranded chain was dissolved in 20 µl of TdT buffer containing 60 µM dCTP and 0.2 µg poly(A). After adding 14 units of TdT (P-L Biochemical), the mixture was incubated at 37° C. for 8 hours to add a (dC) chain of 12 deoxycytidylic acid residues to the 3' end of the cDNA. The reaction product was extracted with phenol-chloroform and precipitated with ethanol to recover a cDNA-vector primer DNA to which a (dC) chain had been added.

The thus obtained (dC) chain-containing cDNA-vector primer DNA was dissolved in 400 µl of a solution (10 mM Tris-HCl, pH 7.5, 6 mM MgCl$_2$, 60 mM NaCl), and 20 units of HindIII was also added. The mixture was incubated at 37° C. for 2 hours to cut the DNA at HindIII site. The reaction product was extracted with phenol-chloroform and precipitated with ethanol. Thus, there was obtained 0.5 pmole of a (dC) chain-containing cDNA-vector primer DNA.

The thus obtained (dC) chain-containig cDNA-vector primer DNA (0.08 pmole) and the aforementioned linker DNA (0.16 pmole) were dissolved in 40 µl of a solution: 10 mM Tris-HCl (pH 7.5), 0.1 M NaCl, 1 mM EDTA. The resulting solution was incubated at 65° C. for 10 minutes, at 42° C. for 25 minutes, and then at 0° C. for 30 minutes. The reaction mixture was adjusted to 20 mM Tris-HCl (pH 7.5), 4 mM MgCl$_2$, 10 mM (NH$_4$)$_2$SO$_4$, 0.1M KCl and 0.1 mM β-NAD in a total volume of 400 μl.

To the reaction mixture, there was added 10 units of E. coli DNA ligase (New England Biolabs), followed by incubation overnight at 11° C. After adjusting the concentrations of dNTP and β-NAD in the reaction mixture to 40 μM and 0.15 mM, respectively, by supplementing necessary reagents, 5 units of E. coli DNA ligase, 7 units of E. coli DNA polymerase I (P-L Biochemicals) and 2 units of E. coli ribonuclease H (P-L Biochemicals) were added to the reaction mixture. The mixture was incubated at 12° C. for one hour and then at 25° C. for one hour.

In the course of the above reactions, a recombinant DNA containing the cDNA was cyclized and the RNA portion of the RNA-DNA double stranded chain was substituted by DNA. Thus, a desired recombinant plasmid containing a complete double-stranded DNA was produced.

The recombinant plasmid was used to transform competent cells of E. coli strain MC1064 prepared by conventional methods. Approximately 50,000 transformants were fixed on a nitrocellulose filter. These colonies were screened according to the colony hybridization method described in Molecular Cloning, Cold Spring Harbor Laboratory, p. 329 et seq. (1982) using the cDNA fragment obtained in Example 1 as a $^{32}$P-labelled probe. Thus, three clones showed strong hybridization at 42° C.

These positive clones were analyzed in detail by Southern method: J. Mol. Biol., 98, 503 (1975). There was obtained the desired full length cDNA of a gene coding for an antigenic protein specific to non-A non-B hepatitis. The base sequence of the cDNA is shown in FIG. 4.

The expression vector containing the full length cDNA was designated as pCDVCL-I.

EXAMPLE 3

Preparation of Expression Vector and Transformant and Expression of Specific Antigen A. Preparation of Expression Vector and Transformant (I) Modification of N-terminus (FIG. 5)

(i) In 100 μl of a buffer (10 mM Tris-HCl, pH 7.5, 100 mM NaCl, 6 mM MgCl$_2$), pCDVCL-I (5 μg) was digested with PvuI (10 units) at 37° C. for 2 hours. The reaction mixture was heated at 75° C. for 15 minutes to deactivate the enzyme, dialyzed against water, and dried. The cleaved plasmid DNA was treated with T4 DNA polymerase (4 units) in 40 μl of a system: 33 mM Tris-acetic acid (pH 7.9), 66 mM potassium acetate, 10 mM magnesium acetate and 0.5 mM dithiothreitol, to which 2 mM 4-deoxytriphosphate had been added; thus, the 3' protruding end of the plasmid DNA was filled in to produce a blunt end. The thus treated mixture was heated at 70° C. for 10 minutes to deactivate the enzyme, dialyzed against water, and dried. The thus obtained plasmid DNA was then stored in the form of an aqueous solution (50 μl). This plasmid DNA fragment is hereinafter designated as Fragment I.

(ii) On the other hand, pCDVCL-I (20 μg) was digested with NcoI and HindIII (each 20 units) at 37° C. for 2 hours in 100 μl of a buffer: 10 mM Tris-HCl (pH 7.5), 100 mM NaCl, 6 mM MgCl$_2$ The plasmid DNA was subjected to 5% acrylamide gel electrophoresis at 10 V/cm for 1.5 hours in a buffer: 89 mM Tris, 89 mM boric acid, 2 mM EDTA. The gel was stained with 0.05% aqueous ethidium bromide solution and two gel slices corresponding to DNA fragments of larger molecular weights were excised from the gel under ultraviolet radiation at 340 nm. The gel slices were crushed by means of a glass rod, suspended into 4 ml of a buffer for DNA extraction (0.5M ammonium acetate, 10 mM magnesium acetate, 1 mM EDTA, 0.1% sodium laurylsulfate), and allowed to stand overnight at 37° C. to extract DNA from the gel. The materials were subjected to centrifugation at 10,000 rpm for 15 minutes to eliminate larger gel pieces, and passed through a glass filter to remove smaller gel pieces. The DNA was purified by effecting ethanol percipitation three times and stored in the form of an aqueous solution (200 μl). This plasmid DNA fragment is hereinafter designated as Fragment II.

(iii) A primer of the DNA portion to be modified as shown below (51 bases) was synthesized by a DNA synthesizer, NIKKAKI (Japan), Applied Biosystem MODEL 380A. The synthesized DNA was overnight reacted with concentrated aqueous ammonia at 55° C. to deprotect and purified by reversed HPLC before use.

```
                        HindIII
Primer        ACAACAGATCTAAGCTTATGGCAGT
                       |          |
                       x    x   x
(Original sequence) (-------------A---A--G----------

TACAACAAGATTAACATGGTTGCATG   wherein x
                             represents a
x     x x  x   x             base substitution.
G-------TC--C---G---------------)
```

The synthetic primer (150 pmole) was treated with T4 polynucleotide kinase (20 units) in 10 μl of a kinase buffer (50 mM Tris-HCl, pH 8.0, 10 mM MgCl$_2$, 5 mM dithiothreitol) to phosphorylate the 5' end thereof.

(iv) Fragment I (0.05 pmole), Fragment II (0.05 pmole) and 5'-phosphorylated primer (45 pmole) were added to 12 μl of 5x polymerase-ligase buffer (0.5 M NaCl, 32.5 mM Tris-HCl, pH 7.5, 40 mM MgCl$_2$, 5 mM β-mercaptoethanol) to make the total volume of the mixture 34.8 μl. The mixture was boiled at 100° C. for 3 minutes, immediately after which it was placed in a thermostat at 30° C. and allowed to stand for 30 minutes. The mixture was allowed to stand at 4° C. for 30 minutes and then on ice for 10 minutes to form a heteroduplex.

To an aqueous solution (11.6 μl) containing the heteroduplex, there were added 2.5 mM 4-deoxynucleotide triphosphate (2 μl), 10 mM ATP (2 μl), Klenow enzyme (2 units) and T4 DNA ligase (0.5 units) to form a mixture of 20 μl in total volume. The mixture was reacted overnight at 16° C. to cyclize the DNA.

An aqueous solution (2 μl) containing the circular DNA was used to transform E. coli HB101 strain according to conventional methods. Plasmids were separated from the transformant and purified in conventional manners. The plasmid was cleaved with restriction enzyme HindIII and subjected to 5% acrylamide gel electrophoresis. Thus, two separate fragments were collected as desired modified, variant plasmids. Since resulting variant plasmids might often be admixed with original wild-type plasmids, the thus obtained variant plasmids were again employed to transform E. coli HB101 so as to purify the plasmid.

Thus, a purified plasmid pCV44H was obtained (FIG. 5).

Figure 6:
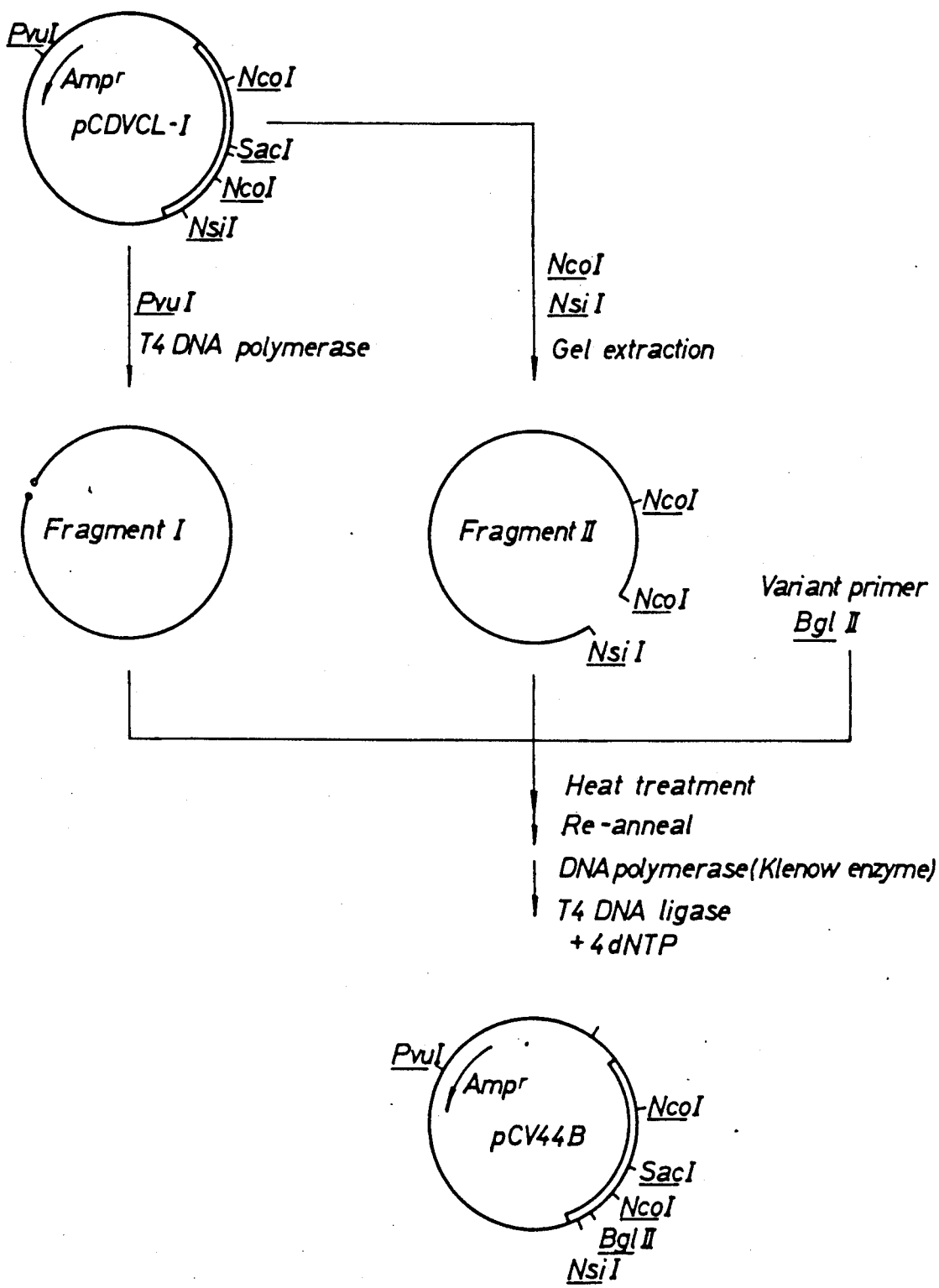
FIG. 6 schematically illustrates the construction of a plasmid pCV44B.

(II) Modification of C-terminus (FIG. 6)

(i) Plasmid pCDVCL-I (5 μg) was treated in the same manner as in I) i) described above to produce Fragment I.

(ii) Plasmid pCDVCL-I (20 μg) was treated in ths same manner as in I) ii) described above except that NcoI and NsiI (each 5 units) were employed. Thus, Fragment II was produced.

(iii) In the same manner as in I) iii) described above, the following primer (46 bases) was synthesized and the 5' end thereof was phosphorylated.

Primer        GCACAAGGAAAAAAAT (Original sequence) (- - - - - - - - - - - - - - - - - - - -)

BglII      SalI                              wherein x
GAGATCTGTCGACGGTTCACGTAAATTTCC    represents
└───┘   └───┘                                a base
                                             substitution
x x x x x x x x x x x x                      and *
AGATATGTGAA* A- - - - - - - - - - - - - - - - - - - -) represents
                                             an addition.

(iv) The Fragment I and II and the 5'-phosphorylated primer obtained above in II) (i) to (iii) were treated in the same manner as in (I) (iv) described above. Thus, plasmid pCV44B was obtained (FIG. 6).

Figure 7:
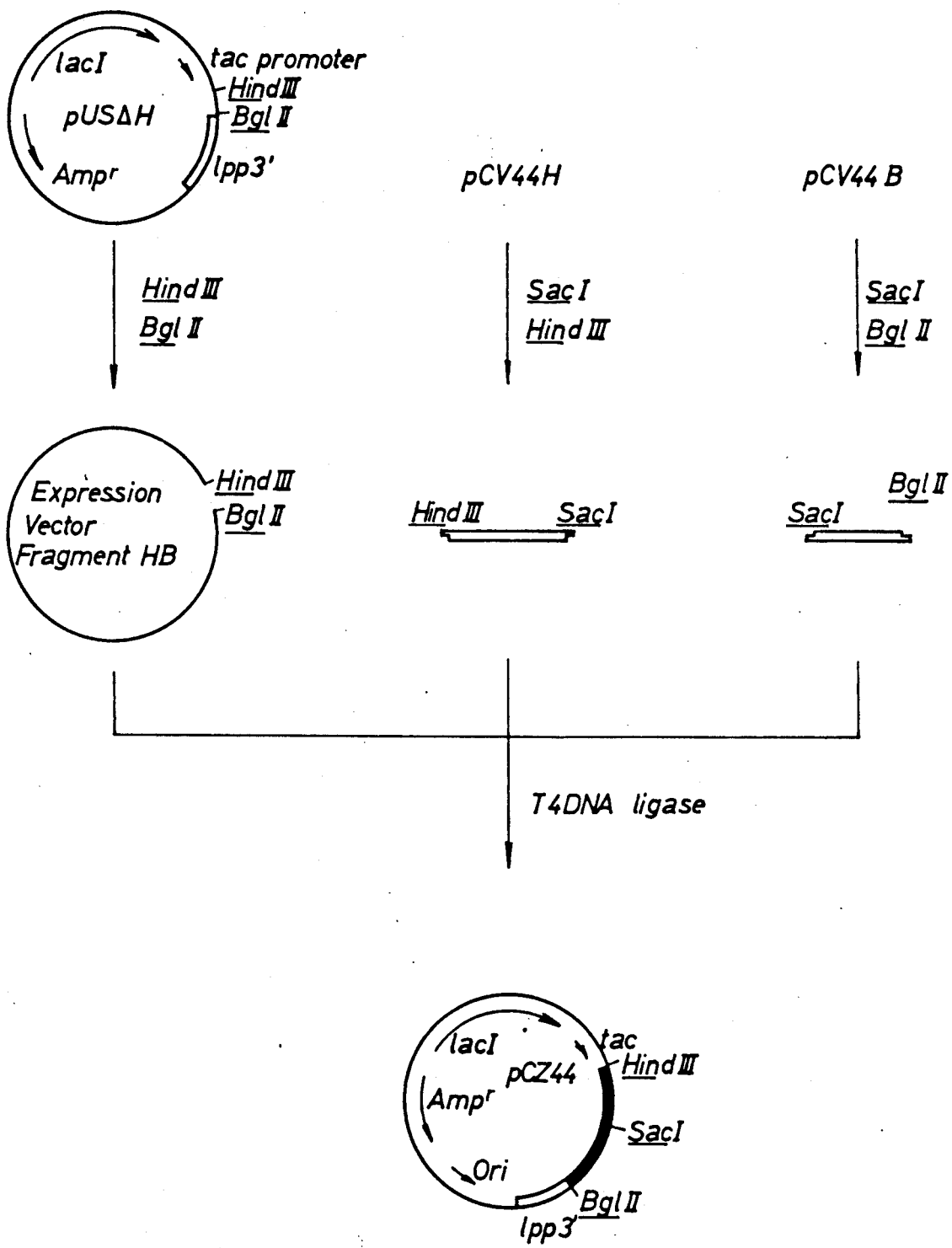
FIG. 7 schematically illustrates the construction of a plasmid pCZ44.

(III) Introduction of cDNA coding for specific antigen into expression vector (FIG. 7)

(i) In 100 μl of a buffer H (10 mM Tris-HCl, pH 7.5, 100 mM NaCl, 6 mM $MgCl_2$), 10 μg (about 3 pmole) of pCV44H was cut with HindIII (20 units) and SacI (20 units) at 37° C. for 2 hours. The reaction mixture was subjected to 5% acrylamide gel electrophoresis. Thus, a 467 bp DNA fragment coding for the N-terminus of the specific antigen was separated and purified. This fragment is hereinafter designated as Fragment N.

(ii) In 100 μl of the buffer H, 10 μg (about 3 pmole) of pCV44B was cleaved with BglII (20 units) and SacI (20 units) at 37° C. for 2 hours. The reaction mixture was subjected to 5% acrylamide gel electrophoresis to isolate and purify a 836 bp DNA fragment coding for the C-terminus of the specific antigen. The thus obtained fragment is hereinafter designated as Fragment C.

(iii) In 20 μl of buffer H, 2 μg (about 1 pmole) of an expression vector pUSΔH was cut with HindIII (2 units) and BglII (2 units) at 37° C. for 2 hours. The reaction mixture was extracted with an equal volume of water-saturated phenol to remove proteins. After extracting the phenol with ether, the reaction mixture was dialyzed against water to desalt, and concentrated by a vacuum pump. Thus, there was obtained 10 μl of an aqueous solution containing an expression vector fragment HB.

(iv) Fragment N (0.5 pmole), Fragment C (0.5 pmole) and the expression vector fragment HB (0.1 pmole) were mixed and reacted with T4 DNA ligase (1 unit) at 4° C. for 16 hours in 10 μl of a buffer (10 mM Tris-HCl, pH 7.5, 1 mM dithiothreitol, 6 mM $MgCl_2$, 1 mM ATP).

The reaction mixture (3 μl) was used to transform commercially available E. coli JM109 competent cell according to conventional methods. The resulting transformants were selected in L broth plate (bactopeptone 10 g, yeast exstract 5 g, NaCl 10 g, agar 15 g per liter) containing 20 μg/ml ampicillin. Thus, there was obtained an expression vector pCZ44 containing the specific antigen gene inserted thereinto (FIG. 7).

B. Expression of Specific Antigen

E coli strain JM109 possessing pCZ44 was cultured over-night at 30° C. in L broth. The culture was inoculated in a fresh L broth with a dilution of 1/50 and cultured with shaking at 30° C. for 2 hours. After IPTG (isopropylthio-β-D-galactopyranoside) was added to the medium in a concentration of 2 mM, shaking culture was continued at 30° C. for further 3 hours. The cells were collected by centrifugation at 6,500 rpm for 10 minutes and suspended in a buffer (0.9% NaCl, 10 mM Tris-HCl, pH 7.5) to store.

C. Verification of Expression of Specific Antigen

The thus obtained cell culture (0.3 ml) was subjected to 10% SDS polyacrylamide gel electrophoresis at 120 V for one hour in a buffer (Tris 3g/l, glycine 14.4 g/l, 0.1% SDS). The gel was removed, placed on a nitrocellulose filter, interposed between filter papers and electrophoresed at 5 V/cm, 4° C. in a buffer (Tris 3g/l, glycine 14.4 g/l) to transferred proteins in the gel onto the nitrocellulose filter. The nitrocellulose filter was rinsed with TBS buffer (10 mM Tris-HCl, pH 7.5, 50 mM NaCl), immersed into 400 ml of TBS buffer containing 3% gelatine and shaked at 40° C. for one hour to block the nitrocellulose filter.

To TBS buffer containing 1% gelatine, there was added a monoclonal antibody directed to a non-A non-B hepatitisspecific antigen ($OC_{280}$=4.3) with a dilution of 1/400. The resulting mixture and the nitrocellulose filter were put into a vinyl bag so that the mixture was present in an amount of 2 ml per filter. Reaction was effected at room temperature for 16 hours. The reaction mixture was washed three times with 400 ml of TBS buffer containing 0.05% Tween 20 for 10 minutes.

To TBS buffer containing 1% gelatine, there was added a labelled secondary antibody, anti-mouse IgG-PAP (horseradish peroxidase, Bio Rad), with a dilution of 1/1000. The resulting mixture and the nitrocellulose filter were put into a vinyl bag so that the mixture was present in an amount of 2 ml per filter. Reaction was effected at room temperature for 2 hours. The reaction mixture was washed three times with 400 ml of TBS buffer containing 0.05% Tween 20 for 10 minutes.

Color formation was effected by immersing the filter into 20 ml of TBS buffer containing 12 mg of 4-chloro-1-naphthol (Bio Rad) and hydrogen peroxide. After completion of color formation, the filter was thoroughly washed with water, put into a vinyl bag containing water, and stored in a dark and cold place.

Such a test effected showed that a protein reacting with the monoclonal antibody was found at the same position (44 Kd) as found in the case of the specific antigen derived from infected chimpanzee liver. This verifies that such a specific antigen can be in fact expressed in E. coli.

What is claimed is:

1. An isolated DNA fragment that contains a base sequence coding for a non-A non-B hepatitis-specific antigenic protein which occurs in cells of liver affected with non-A non-B hepatitis, which protein is represented by the following amino acid sequence:

| | | | | | | | | 10 |
|---|---|---|---|---|---|---|---|---|
| Met | Ala | Val | Thr | Thr | Arg | Leu | Thr | Trp |
| | | | | | | | | 20 |
| | | | | | | | | Leu |
| His | Glu | Lys | Ile | Leu | Gln | Asn | His | Phe |
| | | | | | | | | 30 |
| | | | | | | | | Gly |
| Gly | Lys | Arg | Leu | Ser | Leu | Leu | Tyr | Lys |
| | | | | | | | | 40 |
| | | | | | | | | Gly |
| Ser | Val | His | Gly | Phe | His | Asn | Gly | Val |
| | | | | | | | | 50 |
| | | | | | | | | Leu |
| Leu | Asp | Arg | Cys | Cys | Asn | Gln | Gly | Pro |
| | | | | | | | | 60 |
| | | | | | | | | Thr |
| Leu | Thr | Val | Ile | Tyr | Ser | Glu | Asp | His |
| | | | | | | | | 70 |
| | | | | | | | | Ile |
| Ile | Gly | Ala | Tyr | Ala | Glu | Glu | Gly | Tyr |
| | | | | | | | | 80 |
| | | | | | | | | Gln |
| Glu | Arg | Lys | Tyr | Ala | Ser | Ile | Ile | Leu |
| | | | | | | | | 90 |
| | | | | | | | | Phe |
| Ala | Leu | Gln | Glu | Thr | Lys | Ile | Ser | Glu |
| | | | | | | | | 100 |
| | | | | | | | | Trp |
| Lys | Leu | Gly | Leu | Tyr | Thr | Pro | Glu | Thr |
| | | | | | | | | 110 |
| | | | | | | | | Leu |
| Phe | Cys | Cys | Asp | Val | Ala | Lys | Tyr | Asn |
| | | | | | | | | 120 |
| | | | | | | | | Ser |
| Pro | Thr | Asn | Phe | Gln | Ile | Asp | Gly | Arg |
| | | | | | | | | 130 |
| | | | | | | | | Asn |
| Arg | Lys | Val | Ile | Met | Asp | Leu | Lys | Thr |
| | | | | | | | | 140 |
| | | | | | | | | Met |
| Glu | Asn | Leu | Gly | Leu | Ala | Gln | Asn | Cys |
| | | | | | | | | 150 |
| | | | | | | | | Thr |
| Ile | Ser | Ile | Gln | Asp | Tyr | Glu | Val | Phe |
| | | | | | | | | 160 |
| | | | | | | | | Arg |
| Cys | Glu | Asp | Ser | Leu | Asp | Glu | Arg | Lys |
| | | | | | | | | 170 |
| | | | | | | | | Ile |
| Lys | Gly | Val | Ile | Glu | Leu | Arg | Lys | Ser |
| | | | | | | | | 180 |
| | | | | | | | | Leu |
| Leu | Ser | Ala | Leu | Arg | Thr | Tyr | Glu | Pro |
| | | | | | | | | 190 |
| | | | | | | | | Tyr |
| Gly | Ser | Leu | Val | Gln | Gln | Ile | Arg | Ile |
| | | | | | | | | 200 |
| | | | | | | | | Leu |
| Leu | Leu | Gly | Pro | Ile | Gly | Ala | Gly | Lys |
| | | | | | | | | 210 |
| | | | | | | | | Ser |
| Ser | Phe | Phe | Asn | Ser | Val | Arg | Ser | Val |
| | | | | | | | | 220 |
| | | | | | | | | Phe |
| Gln | Gly | His | Val | Thr | His | Gln | Ala | Leu |
| | | | | | | | | 230 |
| | | | | | | | | Val |
| Gly | Thr | Asn | Thr | Thr | Gly | Ile | Ser | Glu |
| | | | | | | | | 240 |
| | | | | | | | | Lys |
| Tyr | Arg | Thr | Tyr | Ser | Ile | Arg | Asp | Gly |
| | | | | | | | | 250 |
| | | | | | | | | Lys |
| Asp | Gly | Lys | Tyr | Leu | Pro | Phe | Ile | Leu |
| | | | | | | | | 260 |
| | | | | | | | | Cys |
| Asp | Ser | Leu | Gly | Leu | Ser | Glu | Lys | Glu |
| | | | | | | | | 270 |
| | | | | | | | | Gly |
| Gly | Leu | Cys | Met | Asp | Asp | Ile | Ser | Tyr |
| | | | | | | | | 280 |
| | | | | | | | | Ile |
| Leu | Asn | Gly | Asn | Ile | Arg | Asp | Arg | Tyr |
| | | | | | | | | 290 |
| | | | | | | | | Gln |
| Phe | Asn | Pro | Met | Glu | Ser | Ile | Lys | Leu |
| | | | | | | | | 300 |
| | | | | | | | | Asn |
| His | His | Asp | Tyr | Ile | Asp | Ser | Pro | Ser |
| | | | | | | | | 310 |
| | | | | | | | | Leu |
| Lys | Asp | Arg | Ile | His | Cys | Val | Ala | Phe |
| | | | | | | | | 320 |
| | | | | | | | | Val |
| Phe | Asp | Ala | Ser | Ser | Ile | Glu | Tyr | Phe |
| | | | | | | | | 330 |
| | | | | | | | | Ser |
| Ser | Gln | Met | Ile | Val | Lys | Ile | Lys | Arg |
| | | | | | | | | 340 |
| | | | | | | | | Ile |
| Arg | Arg | Glu | Leu | Val | Asn | Ala | Gly | Val |
| | | | | | | | | 350 |
| | | | | | | | | Val |
| His | Val | Ala | Leu | Leu | Thr | His | Val | Asp |
| | | | | | | | | 360 |
| | | | | | | | | Ser |
| Met | Asp | Leu | Ile | Thr | Lys | Gly | Asp | Leu |
| | | | | | | | | 370 |
| | | | | | | | | Ile |
| Glu | Ile | Glu | Arg | Cys | Val | Pro | Val | Arg |
| | | | | | | | | 380 |
| | | | | | | | | Ser |
| Lys | Leu | Glu | Glu | Val | Gln | Arg | Lys | Leu |
| | | | | | | | | 390 |
| | | | | | | | | Gly |
| Phe | Ala | Leu | Ser | Asp | Ile | Ser | Val | Val |
| | | | | | | | | 400 |
| | | | | | | | | Ser |
| Asn | Tyr | Ser | Ser | Glu | Trp | Glu | Leu | Asp |
| | | | | | | | | 410 |
| | | | | | | | | Pro |
| Val | Lys | Asp | Val | Leu | Ile | Leu | Ser | Ala |
| | | | | | | | | 420 |
| | | | | | | | | Leu |
| Arg | Arg | Met | Leu | Trp | Ala | Ala | Asp | Asp |
| | | | | | | | | 430 |
| | | | | | | | | Phe |
| Leu | Glu | Asp | Leu | Pro | Phe | Glu | Gln | Ile |
| | | | | | | | | 440 |
| | | | | | | | | Gly |
| Asn | Leu | Arg | Glu | Glu | Ile | Ile | Asn | Cys | Ala |
| Gln | Gly | Lys | Lys. | | | | | | |

2. The DNA fragment in accordance with claim 1, in which the cells of the liver are derived from a human or chimpanzee individual.

3. The DNA fragment in accordance with claim 1, in which the base sequence comprises the following base sequence:

| | | | 10 | | | 20 |
|---|---|---|---|---|---|---|
| 5' ATG | GCA | GTG | ACA | ACT | CGT | TTG |
| | | 30 | | | | 40 |
| ACA | TGG | TTG | CAT | GAA | AAG | ATC |
| | | 50 | | | 60 | |
| CTG | CAA | AAT | CAT | TTT | GGA | GGG |
| | | 70 | | | 80 | |
| AAG | CGG | CTT | AGC | CTT | CTC | TAT |
| | | 90 | | | 100 | |
| AAG | GGT | AGT | GTC | CAT | GGA | TTC |
| | | 110 | | | 120 | |
| CAT | AAT | GGA | GTT | TTG | CTT | GAC |
| | | 130 | | | 140 | |
| AGA | TGT | TGT | AAT | CAA | GGG | CCT |
| | | 150 | | | 160 | |
| ACT | CTA | ACA | GTG | ATT | TAT | AGT |
| | | 170 | | | 180 | |
| GAA | GAT | CAT | ATT | ATT | GGA | GCA |
| | | 190 | | | 200 | | 210 |
| TAT | GCA | GAA | GAG | GGT | TAC | CAG |
| | | | 220 | | | 230 |
| GAA | AGA | AAG | TAT | GCT | TCC | ATC |
| | | | 240 | | | 250 |
| ATC | CTT | TTT | GCA | CTT | CAA | GAG |
| | | 260 | | | 270 | |
| ACT | AAA | ATT | TCA | GAA | TGG | AAA |
| | | 280 | | | 290 | |
| CTA | GGA | CTA | TAT | ACA | CCA | GAA |
| | | 300 | | | 310 | |
| ACA | CTG | TTT | TGT | TGT | GAC | GTT |
| | | 320 | | | 330 | |
| GCA | AAA | TAT | AAC | TCC | CCA | ACT |
| | | 340 | | | 350 | |
| AAT | TTC | CAG | ATA | GAT | GGA | AGA |
| | | 360 | | | 370 | |
| AAT | AGA | AAA | GTG | ATT | ATG | GAC |
| | | 380 | | | 390 | | 400 |
| TTA | AAG | ACA | ATG | GAA | AAT | CTT |
| | | | 410 | | | 420 |
| GGA | CTT | GCT | CAA | AAT | TGT | ACT |
| | | | 430 | | | 440 |
| ATC | TCT | ATT | CAG | GAT | TAT | GAA |
| | | 450 | | | 460 | |
| GTT | TTT | CGA | TGC | GAA | GAT | TCA |
| | | 470 | | | 480 | |
| CTG | GAC | GAA | AGA | AAG | ATA | AAA |
| | | 490 | | | 500 | |
| GGG | GTC | ATT | GAG | CTC | AGG | AAG |
| | | 510 | | | 520 | |
| AGC | TTA | CTG | TCT | GCC | TTG | AGA |
| | | 530 | | | 540 | |
| ACT | TAT | GAA | CCA | TAT | GGA | TCC |
| | | 550 | | | 560 | |
| CTG | GTT | CAA | CAA | ATA | CGA | ATT |
| | | 570 | | | 580 | |
| CTG | CTG | CTG | GGT | CCA | ATT | GGA |
| | | 590 | | | 600 | |
| GCT | GGG | AAG | TCT | AGC | TTT | TTC |
| 610 | | | 620 | | | 630 |

-continued

| | | | | | | |
|---|---|---|---|---|---|---|
| AAC | TCA | GTG | AGG 640 | TCT | GTT | TTC 650 |
| CAA | GGG | CAT 660 | GTA | ACG | CAT | CAG 670 |
| GCT | TTG | GTG 680 | GGC | ACT | AAT 690 | ACA |
| ACT | GGG | ATA 700 | TCT | GAG | AAG 710 | TAT |
| AGG | ACA 720 | TAC | TCT | ATT | AGA 730 | GAC |
| GGG | AAA 740 | GAT | GGC | AAA 750 | TAC | CTG |
| CCA | TTT 760 | ATT | CTG | TGT 770 | GAC | TCA |
| CTG 780 | GGG | CTG | AGT | GAG 790 | AAA | GAA |
| GGC 800 | GGC | CTG | TGC 810 | ATG | GAT | GAC |
| ATA 820 | TCC | TAC | ATC 830 | TTG | AAC | GGT 840 |
| AAC | ATT | CGT | GAT 850 | AGA | TAC | CAG 860 |
| TTT | AAT | CCC 870 | ATG | GAA | TCA | ATC 880 |
| AAA | TTA | AAT 890 | CAT | CAT | GAC 900 | TAC |
| ATT | GAT | TCC 910 | CCA | TCG | CTG 920 | AAG |
| GAC | AGA 930 | ATT | CAT | TGT | GTG 940 | GCA |
| TTT | GTA 950 | TTT | GAT | GCC 960 | AGC | TCT |
| ATT | GAA 970 | TAC | TTC | TCC 980 | TCT | CAG |
| ATG 990 | ATA | GTA | AAG 1000 | ATC | AAA | AGA |
| ATT 1010 | CGA | AGG | GAG 1020 | TTG | GTA | AAC 1030 |
| GCT | GGT | GTG | GTA 1040 | CAT | GTG | GCT 1050 |
| TTG | CTC | ACT 1060 | CAT | GTG | GAT | AGC 1070 |
| ATG | GAT | CTG 1080 | ATT | ACA | AAA | GGT 1090 |
| GAC | CTT | ATA 1100 | GAA | ATA | GAG 1110 | AGA |
| TGT | GTG 1120 | CCT | GTG | AGG | TCC 1130 | AAG |
| CTA | GAG 1140 | GAA | GTC | CAA 1150 | AGA | AAA |
| CTT | GGA 1160 | TTT | GCT | CTT 1170 | TCT | GAC |
| ATC | TCG 1180 | GTG | GTT | AGC 1190 | AAT | TAT |
| TCC 1200 | TCT | GAG | TGG 1210 | GAG | CTG | GAC |
| CCT 1220 | GTA | AAG | GAT 1230 | GTT | CTA | ATT 1240 |
| CTT | TCT | GCT | CTG 1250 | AGA | CGA | ATG 1260 |
| CTA | TGG | GCT 1270 | GCA | GAT | GAC | TTC 1280 |
| TTA | GAG | GAT 1290 | TTG | CCT | TTT 1300 | GAG |
| CAA | ATA | GGG 1310 | AAT | CTA | AGG 1320 | GAG |
| GAA | ATT 1330 | ATC | AAC | TGT | GCA | CAA |
| GGA | AAA | AAA 3′ | | | | |

4. An expression vector comprising a promoter, a ribosome binding sequence and a base sequence coding for a non-A non-B hepatitis-specific antigen as recited in claim 1 at a cloning site present downstream from the promoter such that transcription of said base sequence is initiated by said promoter.

5. The expression vector in accordance with claim 4 additionally comprising a repressor gene which codes for a repressor of said promoter.

6. The expression vector in accordance with claim 4, in which the promoter operates in a microorganism.

7. The expression vector in accordance with claim 4, in which the promoter operates in an eukaryote.

8. A transformant obtained by transforming a host with an expression vector, said expression vector comprising a promoter, a ribosome binding sequence, and a base sequence coding for a non-A non-B hepatitis-specific antigen as recited in claim 1 at a cloning site present downstream from said promoter such that transcription of said base sequence is affected by said promoter.

9. The transformant in accordance with claim 8, in which the host is *Escherichia coli* or *Bacillus subtilis*.

10. A process for producing an antigen specific to non-A non-B hepatitis, comprising the steps of:
   introducing a promoter, a ribosome binding sequence, and a base sequence coding for an antigen as recited in claim 1 into an expression vector, said base sequence being downstream from said promoter, such that transcription of said base sequence is initiated by said promoter,
   introducing the expression vector containing said DNA fragment into a host,
   culturing said transformed host, and
   collecting the antigen produced by said host.

11. An expression vector as claimed in claim 4, additionally comprising a transcription terminator downstream of said base sequence.

12. A process as claimed in claim 4, additionally comprising the step of introducing a transcription terminator downstream of said base sequence.

* * * * *